(12) United States Patent
Polikhov

(10) Patent No.: US 9,086,306 B2
(45) Date of Patent: Jul. 21, 2015

(54) APPARATUS AND METHOD FOR MEASURING MULTI-PHASE FLUID FLOW

(75) Inventor: Stepan Polikhov, Ramenskoe (RU)

(73) Assignee: SIEMENS AKTIENGESELLSCHAFT, München (DE)

( * ) Notice: Subject to any disclaimer, the term of this patent is extended or adjusted under 35 U.S.C. 154(b) by 348 days.

(21) Appl. No.: 13/382,165

(22) PCT Filed: Jul. 7, 2009

(86) PCT No.: PCT/RU2009/000340
§ 371 (c)(1),
(2), (4) Date: Jan. 4, 2012

(87) PCT Pub. No.: WO2011/005133
PCT Pub. Date: Jan. 13, 2011

(65) Prior Publication Data
US 2012/0114097 A1    May 10, 2012

(51) Int. Cl.
*G01N 23/04* (2006.01)
*G01F 1/74* (2006.01)
*G01N 23/12* (2006.01)
(Continued)

(52) U.S. Cl.
CPC *G01F 1/74* (2013.01); *G01F 1/704* (2013.01); *G01N 23/04* (2013.01); *G01N 23/087* (2013.01); *G01N 23/12* (2013.01); *G01N 2223/423* (2013.01); *G01N 2223/635* (2013.01); *G01N 2223/637* (2013.01)

(58) Field of Classification Search
CPC ........ G01F 1/74; G01N 23/04; G01N 23/087; G01N 23/12; G01N 2223/423; G01N 2223/635; G01N 2223/637
USPC .......... 378/51, 52, 53, 54; 250/356.1
See application file for complete search history.

(56) References Cited

U.S. PATENT DOCUMENTS

| | | | | |
|---|---|---|---|---|
| 4,200,797 A | * | 4/1980 | Bax | 378/15 |
| 5,025,160 A | * | 6/1991 | Watt | 250/356.1 |

(Continued)

FOREIGN PATENT DOCUMENTS

| | | | |
|---|---|---|---|
| EP | 1760458 A1 | * | 3/2007 |
| GB | 2356453 A | | 5/2001 |

(Continued)

OTHER PUBLICATIONS

Bin Hu et al: "Development of an X-ray computed tomography (CT) system with sparse sources: application to three-phase pipe flow visualization", Experiments in fluids; Experimental methods and their applications to fluid flow, 2005; pp. 667-678; vol. 39, No. 4, XP019338257; Springer, Berlin.

*Primary Examiner* — Glen Kao

(57) ABSTRACT

An apparatus and method are provided for measuring flow velocity of a multi-phase fluid mixture. The proposed apparatus includes a radiation device, a detection device, and an analysis device. The radiation device generates a beam of photons to irradiate the mixture spatially over a section of flow of the mixture. The detection device is spatially configured to receive photons emanating from the section of flow of the mixture at different intervals of time. The detection device provides an image of a spatial distribution of the received photons for each the interval of time. The analysis device determines flow velocity of one or more phases of the mixture based on a temporal sequence of the images of the spatial distributions of the received photons.

13 Claims, 3 Drawing Sheets

(51) Int. Cl.
  *G01N 23/087* (2006.01)
  *G01F 1/704* (2006.01)

(56) References Cited

U.S. PATENT DOCUMENTS

| 6,400,792 | B1* | 6/2002 | Misawa | 378/19 |
| 2006/0203961 | A1* | 9/2006 | Morton | 378/57 |
| 2007/0206179 | A1 | 9/2007 | Hong | |

FOREIGN PATENT DOCUMENTS

| RU | 2122724 C1 | 11/1998 |
| RU | 2334251 C1 | 9/2008 |
| RU | 2334972 C2 | 9/2008 |
| WO | WO 9118280 A1 | 11/1991 |
| WO | WO 03106934 A1 | 12/2003 |

* cited by examiner

APPARATUS AND METHOD FOR MEASURING MULTI-PHASE FLUID FLOW

CROSS REFERENCE TO RELATED APPLICATIONS

This application is the US National Stage of International Application No. PCT/RU2009/000340, filed Jul. 7, 2009 and claims the benefit thereof. The International Application is incorporated by reference herein in their entirety.

FIELD OF INVENTION

The present invention relates flowmeters for measuring flow of multi-phase mixtures. Embodiments of the present invention may find application, for example, in the oil and gas industry, where a mixture of liquid hydrocarbons and gaseous hydrocarbons is of concern.

BACKGROUND OF INVENTION

The problem of measuring the flow-rates of multi-phase fluids in a pipe without the need to interrupt fluid flow or separate the phases during the measurement process is of particular importance in the chemical and petroleum industries. Because almost all wells produce a mixture of oil, water, and gas, flow measurements of the individual components of the fluid mixture are essential in the efficient production of a reservoir. Conventionally, at the surface, these measurements were made through separators, which are costly and bulky, especially for offshore applications.

The above problem has been addressed by multi-phase flow-meter devices which are now commonly used in the oil and gas industry and other chemical industries. Such devices measure flow velocity of various components of a multi-phase fluid mixture by measurement of Gamma ray or X-ray attenuation through the mixture at two different energy levels, namely, a "high" energy level and a "low" energy level. The measurements are based on the fact that the absorption coefficient of the Gamma ray/X-ray radiation is dependent on the material and the photon energy. Accordingly, the "high" energy level is determined such the photon absorption coefficient at this energy level of photons is substantially the same for oil and water. The "low" energy level is determined such the photon absorption coefficient at this energy level of photons is significantly higher for water than for oil. The Gamma rays/X-rays pass through the mixture in a test section of the pipe and irradiate detectors that are sensitive to photons at these two energy levels. Analysis of the signals recorded by the detectors allows evaluation of water, oil and gas flow-rates passing though the test section.

The volumetric flow-rate calculations in such prior art devices are based on pressure differential measurements, for which reason, the test section is provided with a contraction, such as a Venturi restriction. A Venturi restriction interferes with the fluid flow. Further, such an arrangement provides limited precision in flow measurements and is particularly disadvantageous in case of non-uniform flow composition, in particular, across the cross-section of the mixture flow.

SUMMARY OF INVENTION

The object of the present invention is to provide an improved apparatus and method for measurement multi-phase fluid flow.

The above object is achieved by the features of the independent claims.

The underlying idea of the present invention is to directly measure flow velocity of one or more phases of the mixture based on a temporal sequence of the spatial distribution of photons emanating from the mixture that are received by the detection means. The radiation means is accordingly adapted to provide spatial irradiation of the mixture along the direction of mixture flow, while the detection means is configured for spatially receiving the photons emanating from the mixture. This arrangement thus measures volumetric flow velocity directly without the need for subjecting the mixture flow to a pressure drop by introducing a contraction, such as a Venturi restriction to the mixture flow.

In a preferred embodiment, said detection means comprises a two-dimensional array of detector elements. This embodiment advantageously allows measurement of a spatial density distribution of the mixture transverse to the direction of flow of the mixture.

In a further advantageous embodiment, the proposed apparatus further comprises a measurement tube forming a conduit for said section of flow of the mixture, said measurement tube having a rectangular cross-section. Having a rectangular cross-section of the measurement tube provides convenient processing of the images to measure spatial density distributions of the various phases across the section of the mixture flow.

In an exemplary embodiment, to provide suitable spatial irradiation of the mixture, the radiation means is located at a distance greater than 0.3 m from section of flow of the mixture.

In one embodiment, said analysis means is adapted to determine the flow velocity of one or more phases of said mixture based on cross-correlation of said temporal sequence of images of the spatial distributions of received photons.

In a preferred embodiment, said radiation means is adapted to generate photons at a first energy level and a second energy level, wherein for the first energy level, the photon absorption coefficients for two different phases contained in said mixture are substantially equal, and wherein for the second energy level, the photon absorption coefficients for said two phases of said mixture are different. For a three-phase mixture having two liquid phases and one gaseous phase, the photons having the first energy level thus assist indicating the collective density of the liquids in the mixture, thus assisting identifying the proportion of the gas in the mixture flow. On the other hand, the photons having the second energy level assist indicating the density difference between the liquid phases, thus assisting identifying the relative proportions of the two liquid phases.

In a preferred further embodiment, said radiation generation means is adapted for alternatingly generating first and second pulses of photons, wherein the photons in said first pulse has said first energy level and the photons in said second pulse has said second energy level. This embodiment uses a pulsed power supply that advantageously provides low overall power consumption while providing large instantaneous power during the pulse.

To provide direct measurement of velocity of all phases of the mixture, said detection means is adapted for alternatingly forming first and second images, said first image corresponding to the spatial distribution of received photons having said first energy level during a first interval of time that corresponds to the duration of said first pulse, said second image corresponding to the spatial distribution of received photons having said second energy level during a second interval of time that corresponds to the duration of said first pulse.

In an exemplary embodiment, said photons are X-ray photons. Utilizing X-ray for measurements is advantageous since it does not require radioactive materials which require additional safety measures and may also cause significant problems with import/export operations.

BRIEF DESCRIPTION OF THE DRAWINGS

The present invention is further described hereinafter with reference to illustrated embodiments shown in the accompanying drawings, in which.

DETAILED DESCRIPTION OF INVENTION

Embodiments of the present invention described below provide direct measurement of volumetric flow velocity of the individual phases of a multi-phase mixture by taking into account spatial fluid flow over a section, instead of along a single point beam through the cross-section of the flow as taught in the prior art. The multi-phase mixture may be a mixture of gas (e.g. gaseous hydrocarbons), water, and/or oil (e.g. liquid hydrocarbons). An individual phase may be one of these components. By irradiating the mixture over the entire cross-section of the mixture flow, the spatial density distribution of the phases transverse to the flow direction can be determined, which improves the quality and accuracy of the volumetric flow measurements.

Figure 1:
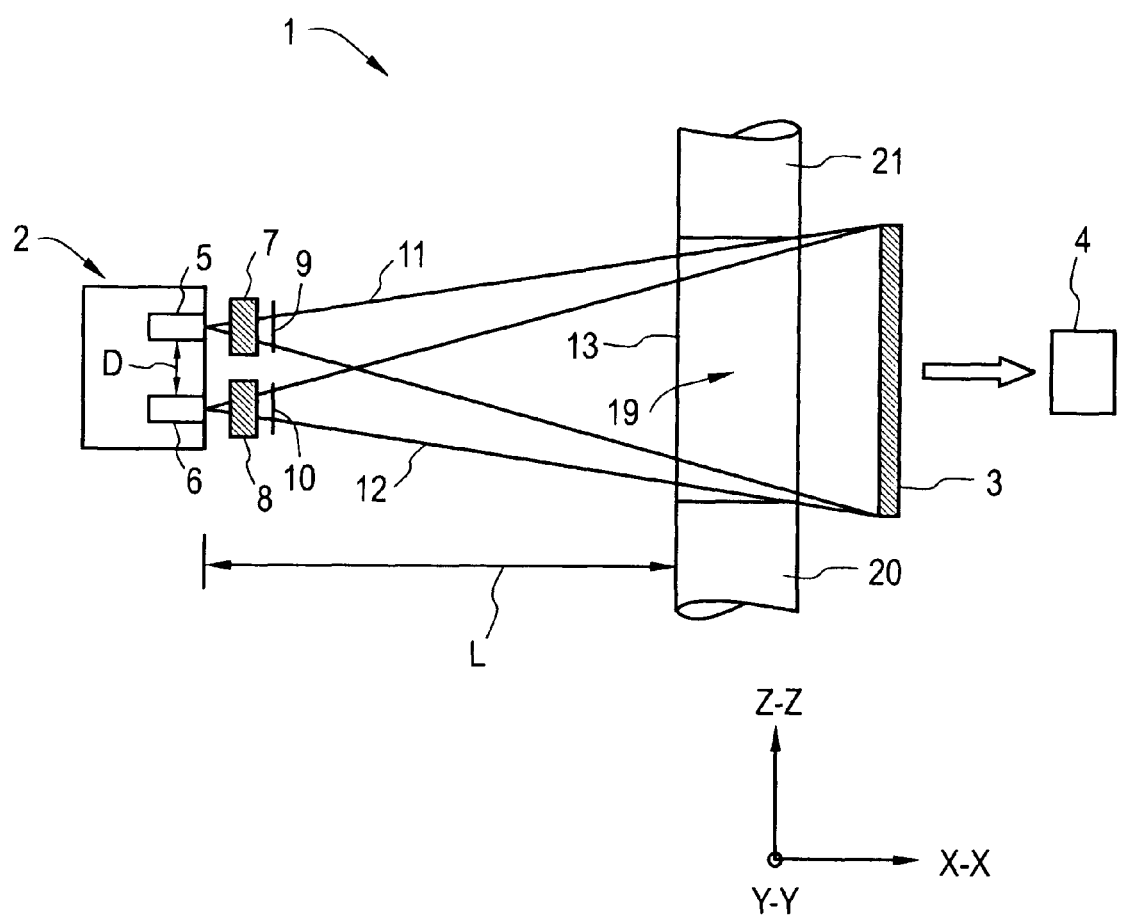
FIG. 1 is a schematic diagram of an apparatus for measuring multi-phase fluid flow.

Referring now to FIG. 1, an apparatus 1 for measurement of multi-phase fluid flow is illustrated in accordance with one embodiment of the present invention. The apparatus 1 may also be referred to as a multi-phase flowmeter. The apparatus 1 broadly includes radiation means 2, detecting means 3 and analysis means 4. The illustrated apparatus 1 also includes a measurement tube 13, which may, for example, be interposed between upstream and downstream pipes 20 and 21 respectively through which flows a multi-phase fluid mixture whose flow rate is to be measured. The multi-phase fluid mixture may particularly be a mixture that occurs especially in upstream oil and gas business. The measurement tube 13 forms a conduit for a section 19 of the mixture flow. In the context of the present discussion, the section 19 may refer to the volume of the mixture within the measurement tube 13 or a portion thereof. The section 19 is also referred to herein as "test section".

The radiation means 2 generates a beam of photons to irradiate said mixture spatially along the test section 19. The photon beam is attenuated upon passing though the mixture. The detection means 3 is configured to spatially receive photons emanating from the test section 19 of flow of the mixture at different intervals of time. The detection means 3 thus forms an image of a spatial distribution of the received photons for each said interval of time. The analysis means 4 determines flow velocity of one or more phases of the mixture based on a temporal sequence of the images of the spatial distributions of the photons received by the detection means 3.

Figure 2:
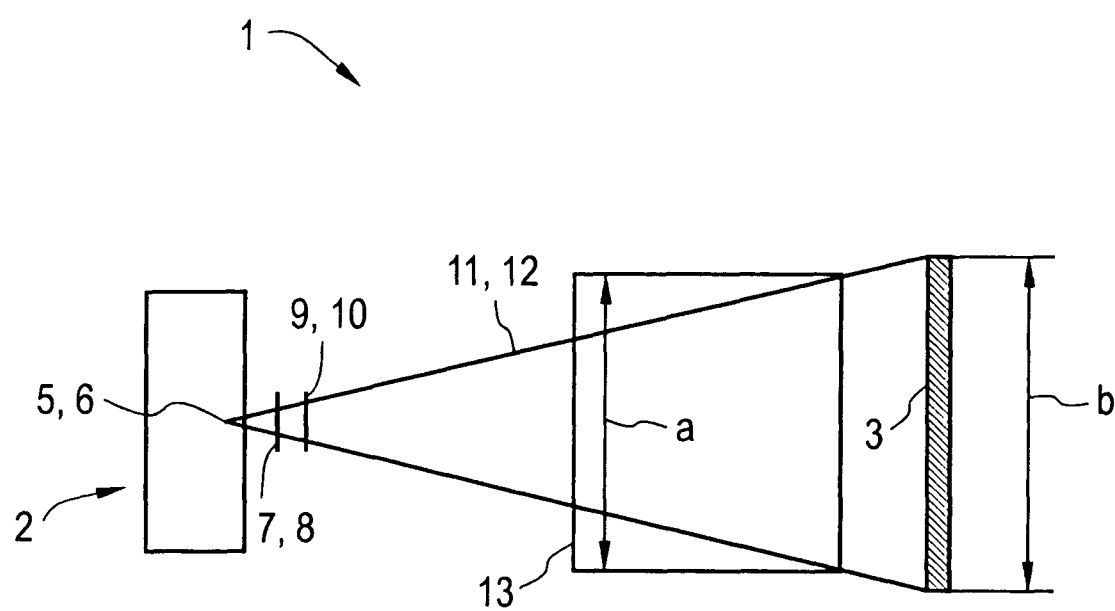
FIG. 2 is a top view of an apparatus for measuring multi-phase fluid flow having two-dimensionally arranged detectors according to one embodiment of the present invention.
Figure 2:
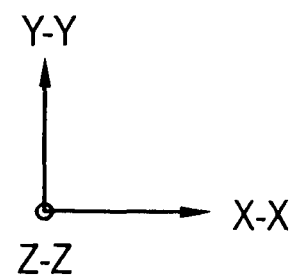
Figure 3:
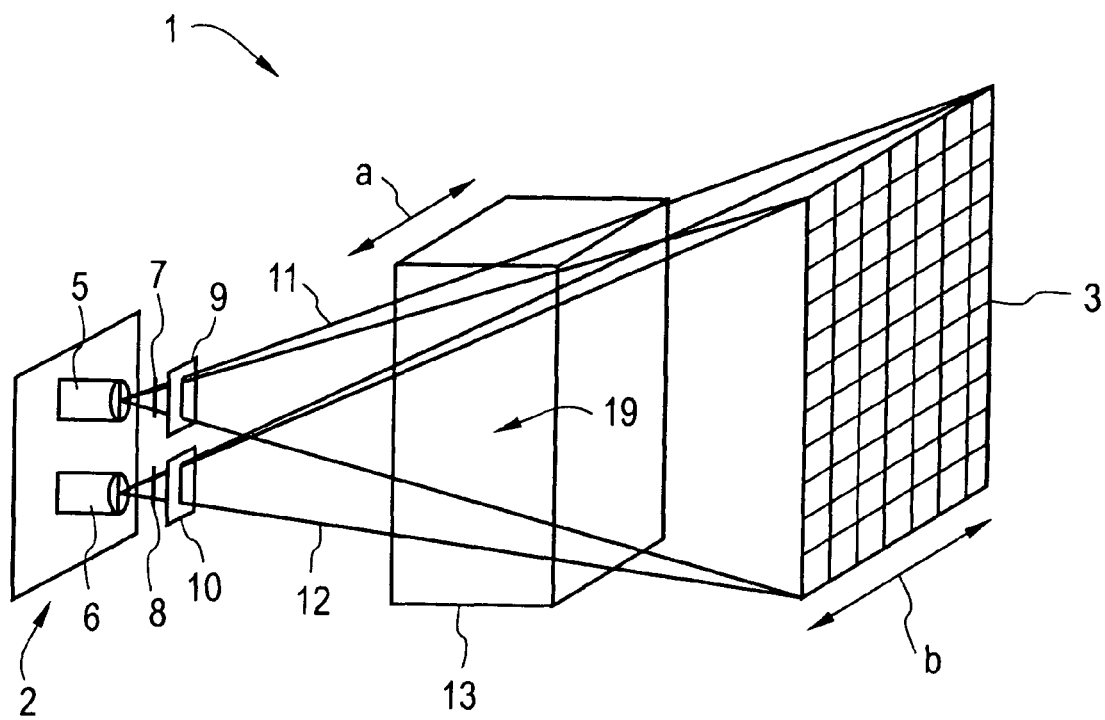
FIG. 3 is a perspective view of the apparatus shown in FIG. 2.
Figure 3:
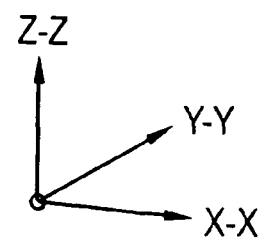

Individual components of the apparatus 1 are discussed in detail below generally referring to FIGS. 1-3, wherein FIG. 2 is a top view depiction of the radiation means 2, detection means 3 and the measurement tube 13 and FIG. 3 is a perspective depiction of the same. FIGS. 1-3 are illustrated with respect to mutually perpendicular axes X-X, Y-Y and Z-Z. The axis Z-Z extends along a flow direction of the mixture, the axis X-X extends along lateral direction generally along the direction of travel of the photon beam and the axis Y-Y extends along a transverse direction across the section 19 of mixture flow.

In the illustrated embodiment, the measurements are done using X-ray photons, which is advantageous since X-ray generation does not require radioactive materials which require additional safety measures and may also cause significant problems with import/export operations. Accordingly, the radiation means 2 includes one or more X-ray tubes. In the shown embodiment, two X-ray tubes 5 and 6 are provided. The X-ray tubes 5 and 6 used in connection with the present invention should preferably deliver a consistent Bremsstrahlung spectrum, especially with a stable endpoint voltage. The X-ray tube 5 generates a beam 11 of X-ray photons at a first energy level while the X-ray tube 6 generates a beam 12 of X-ray photons at a second energy level. The energy levels are chosen such that the first energy level provides sensitivity to the overall density of the mixture whereas the second energy level provides sensitivity to the composition of the mixture. For example, for flow measurement in an effluent flow regime comprising three phases including water, oil and gas, the first energy level is chosen such that the photon absorption coefficients for the liquid phases, i.e., water and oil, are substantially constant for photons at this energy level, while the second energy is chosen such that for photons at this energy level, the photon absorption coefficients for water and oil are significantly different. The photon absorption coefficient of the gaseous phase under the given circumstances is much lower in comparison to that of water and oil. In the above example, the first energy level may fall, for example, in the range 65-90 keV, while the second energy level may fall, for example, in the range of 15-35 keV. Thus in this context, the first energy level is referred to as a "high" energy level while the second energy level is referred to as a "low" energy level. Accordingly in this embodiment, the X-ray tube 5 provides a characteristic emission in the range 65-90 keV, while the X-ray tube 6 provides a characteristic emission in the range 15-35 keV. In a preferred embodiment, the photon beams 11 and 12 from the X-ray tubes 5 and 6 respectively pass through filters 7 and 8 to rule out possible spectral overlapping between the two photon beams. The filters 7 and 8 accordingly should allow maximum transmission within 65-90 keV and 15-35 keV respectively.

The power supplies used in connection with the present invention may be AC or DC. The X-ray tubes 5 and 6 may be operated in a continuous mode but preferably in a pulsed mode. Using a pulsed power supply advantageously leads to lesser overall power consumption and provided higher instantaneous power during the pulses. In the illustrated embodiment, the X-ray tubes 5 and 6 are pulsed alternatingly with an adjustable time delay. The duration of the pulses may be based, for example, on the expected velocity range of the mixture flow, to ensure that the fluid (mixture) does not cover significant distance during the irradiation. For example, in an application where the flow velocity is expected to be 10 m/s or greater with an upper limit of 40 m/s, the pulse duration for each of the X-ray tubes 5 and 6 is preferably lesser than 10 µs. The timing of operation of the X-ray tubes 5 and 6 may, in this case, be adjustable within the limits 0.3-1 ms, with a precision less than 10 µs. In the illustrated embodiment, volumetric flow velocity is measured by cross-correlation analysis (discussed below). Hence the above-mentioned time delay should be adjusted to optimize the quality of the velocity measurements. The voltage applied to the X-ray tubes should be preferably adjustable within 40-70 kV for the "low" energy X-rays and within 130-170 kV for the "high" energy X-rays.

While operating the X-ray tubes 5 and 6 in pulsed mode, it is necessary to ensure that the signal (attenuated photon beam) reaching the detecting means 3 is strong enough. Hence advantageously, the anode material of the "high" energy X-ray tube 5 may include gold (Au) while the anode material of the "low" energy X-ray tube 6 may include molybdenum (Mo).

In an alternate embodiment, instead having two separate X-ray tubes, the radiation means 2 may include a single X-ray tube with two anodes, which may be operated in a continuous or pulsed manner. In a still alternate embodiment, the measurements may be done using other types of photons, such as Gamma rays. Accordingly the radiation means 2 in this case would include one or more Gamma ray radiation sources, for example Cesium 137 or Gadolinium 153 radioisotopes, among others.

In the illustrated embodiment, the photon beams 11 and 12 further pass though beam shaping apertures 9 and 10 respectively which provide a desired shape or cross-section to the beams. The photon beams 11 and 12 passing through the apertures 9 and 10 irradiate the test section 19 of the mixture flow spatially. In the illustrated embodiment, the spatial irradiation of the test section 19 is along the Z-Y plane (i.e., spatially along the flow direction and transverse to the flow direction), as illustrated in FIGS. 2 and 3. This, in conjunction with two dimensional detection means (discussed later) enables measurement of spatial density distribution of the phases of the mixture transverse to the direction of mixture, which is particularly useful for accurately measuring flow velocity in case of non-uniform flow, i.e. fluid flow having non-uniform composition of phases across the cross-section of flow. The photon beams 11 and 12, in this case, would have a two-dimensional beam cross-section. However, the cross-section of the photon beams 11 and 12 may alternatively be one dimensional (i.e., line X-rays) to spatially irradiate the mixture along the Z-Z axis, i.e, the flow direction. This embodiment can be used in case of uniform mixture flow (i.e. for uniform composition of phases across the cross-section of flow) by measuring flow velocity of the individual phases, for example, along the center line of the test section 19. In such a case, the detection means 3 may be adapted for one-dimensional spatial detection of photons.

In one embodiment, the radiation means 2 is located at a distance 'L' from the test section 19 and not attached to the measurement tube 13 as it is conventionally done. This allows the divergent photon beams to sufficiently irradiate the test section 19 of fluid flow. This distance 'L' is typically greater than 0.3 m and preferably about 0.5 m. Since the flow velocity is determined by cross-correlating the images of both the photon beams 11 and 12, the distance 'D' between the X-ray tubes 5 and 6 should be preferably much lesser than the distance 'L' between the radiation means 2 and the test section 19. As an example, distance 'D' may be about 30-70 mm.

The measurement tube 13 includes windows made of a material that is generally transparent to the irradiation by the photon beams 11 and 12. A preferred material used for such a window is beryllium. Although the measurement tube 13 may have any cross-section, a rectangular (which includes square) cross-section of the measuring tube 13 is particularly advantageous in case of non-uniform mixture flow for providing ease of processing of the spatial images acquired by the detection means 3 for measurement spatial density distributions of the various phases across the section 19 of the mixture flow.

The photons beams 11 and 12 are attenuated upon passing through the mixture. The detection means 3 is accordingly spatially configured to receive the photons emanating from the mixture. In case of flow measurement concerning mixtures having uniform composition of phases across the section of flow, it may be sufficient to spatially configure the detection means 3 to receive photons along one dimension. In such a case, the detection means 12 may include a linear array of detector elements aligned along the Z-Z direction, i.e. parallel to the direction of mixture flow. However, for flow measurement concerning mixtures having non-uniform composition of phases across the section of flow, it is advantageous to spatially configure the detection means 3 two-dimensionally, as illustrated in FIGS. 2 and 3. Herein, the detection means 3 includes a two-dimensional array of detector elements or a set of detector elements arranged over a two-dimensional area. The array of detector elements is arranged parallel to the Z-Y plane. The dimension 'b' of the detector array is preferably equal to or greater than the dimension 'a' of the measurement tube 13. The detector elements may include, for example, scintillators, which may include inorganic or organic scintillator crystals, organic liquid scintillators or even plastic scintillators. The detector elements should be sensitive to photons at the above mentioned "high" and "low" energy levels. An exemplary inorganic scintillator that may be used herein as a detector element is NaI crystal. The detector array may comprise associated photomultipliers for generating signals corresponding to the irradiation of the detector elements.

The detection means 3 receives photons for different intervals of time and for each interval of time, forms an image of the spatial distribution of photons received during that interval of time. In the embodiment illustrated herein, the detection means 3 alternatingly forms first and second images of such spatial distributions of the received photons during respective first and second intervals of time corresponding to the pulse duration of the "high" energy and "low" energy photons. Thus, for use in the above mentioned exemplary embodiment, the detector elements should be capable of capturing two images with exposure time less than 10 μs with a time delay less than 0.3 ms. For greater measurement accuracy, the detectors should preferably provide an image resolution of 1000×2000 pixels or higher.

The arrangement of the detection means 3 described above is exemplary. Many alternate embodiments may be considered. For example, the detection means 2 may include two layers of detector arrays arranged back to back, wherein the detector elements in one layer is sensitive to the "high" energy photons while the detector elements in the other layer is sensitive to the "low" energy photons.

The detection means 3 is thus adapted to feed a temporal sequence of images to the analysis means 4 (FIG. 1) for determination of flow velocity of one or more phases of the mixture, each image representing a spatial distribution of photons received in a given interval of time. Depending on the spatial arrangement of detectors, these images may be one-dimensional or two-dimensional. The analysis means 4 may include, for example, a commercial personal computer such as a desktop or a notebook running a program for computation of volumetric and/or mass flow rate of the mixture using the image sequence received from the detection means 3 and for delivering the looked-for results. An example of such a computation is provided below. Depending on the amount of processing required, the analysis means 4 may alternately include a general purpose microprocessor, a field programmable gate array (FPGA), a microcontroller, or any other hardware that comprises processing circuitry and input/output circuitry suitable for computation of flow velocity based on the images received from the detection means 3.

An example of flow velocity computation in the above-mentioned effluent flow regime comprising three phases, namely water, oil and gas is now described. Such a flow regime includes alternating portions made up essentially of gas and portions made up essentially of liquid (water and oil). Since the absorption coefficients of "high" energy photons by water and oil are substantially equal and the absorption coefficient of "high" energy photons by gas in negligible, the temporal sequence of images corresponding to the "high" energy photon pulses are used to determine by what distance the liquid phases as a whole (i.e., oil and water) have traveled in a given interval of time along the flow direction (Z-Z). Advantageously, by using a two-dimensional detector array as in the illustrated embodiment, it is further possible to determine the displacements of the liquid phases as a whole (water and oil) transverse to the flow direction (i.e., along both Z-Z and Y-Y directions).

On the other hand, since the absorption coefficients of "low" energy photons by water and oil are significantly different, an image corresponding to the "low" energy photon pulse can be used to determine the relative proportions water and oil in the mixture, for example, by computing a water-to-liquid ratio (WLR). Thus a temporal sequence of images corresponding to "low" energy pulses would indicate the rate of change of composition (for example, WLR) of the liquid phases along the direction of flow (Z-Z). Again, by using of two-dimensional detector array in accordance with the illustrated example, it is advantageously further possible to determine this rate of change composition of the liquid phases transverse to the direction of flow (i.e., along both Z-Z and Y-Y directions). The volumetric velocity of the individual phases of water and/or oil are computed by cross-correlating the sets of images corresponding to the "high" energy pulse and "low" energy pulses. The time delay between the "high" energy and "low" energy pulses should be accordingly kept as low as permitted by the system. As mentioned above, the time delay in the exemplary embodiment is 0.3-1 ms.

Typically, such multiphase flow involves a disperse mode flow, wherein the average velocities of oil, water and gas are substantially the same under the given conditions. Hence, the volumetric flow rate of all the phases may be obtained by measurement of volumetric flow velocity of one of the phases as described above. The mass flow rate of these phases can be subsequently obtained from the computed volumetric flow velocities by multiplying these quantities by the densities of the respective phases.

Although the invention has been described with reference to specific embodiments, this description is not meant to be construed in a limiting sense. For example, the proposed technique may be used for directly measuring volumetric flow velocities of multi-phase mixtures containing more than or less than three phases, by incorporating appropriate one or more energy levels of photon radiation that provide similar or different absorption properties for two or more phases of the mixture. The photon radiation may then be accordingly pulsed and/or filtered. It is therefore contemplated that all such modifications that essentially determine volumetric flow velocity of a multi-phase mixture based on a temporal sequence of spatially distribution of photons emanating from the irradiated mixture lie within the scope of the present invention defined by the below-mentioned patent claims.

The invention claimed is:

1. An apparatus for measurement of flow velocity of a multi-phase fluid mixture comprising at least a gaseous phase and a liquid phase, the apparatus comprising:

an X-ray radiation device for generating a beam of photons to irradiate the mixture spatially along a section of flow of the mixture, wherein the X-ray radiation device generates photons at a first energy level and a second energy level, wherein for the first energy level, the photon absorption coefficients for two different phases contained in the mixture are substantially equal, and wherein for the second energy level, the photon absorption coefficients for the two phases of the mixture are different, a detection device comprising a single two-dimensional array of detector elements arranged on a single plane, wherein the single two-dimensional array of detector elements is spatially configured for receiving photons that are generated at both the first and second energy levels upon emanating from the section of flow of the mixture over a two-dimensional area along the plane at different intervals of time, and for forming a two-dimensional image of a spatial distribution of the received photons for each said interval of time, and an analysis device for determining a flow velocity of each of the phases of the fluid mixture based on a temporal sequence of the images of the spatial distributions of the received photons, wherein the plane extends along a first direction parallel to a flow direction of the mixture and a second direction transverse to the flow direction.

2. The apparatus according to claim 1, further comprising a measurement tube forming a conduit for the section of flow of the mixture, the measurement tube having a rectangular cross-section.

3. The apparatus according to claim 1, wherein the X-ray radiation device is located at a distance greater than 0.3 m from the section of flow of the mixture.

4. The apparatus according to claim 1, wherein the analysis device determines the flow velocity of one or more phases of the mixture based on cross-correlation of the temporal sequence of images of the spatial distributions of received photons.

5. The apparatus according to claim 1, wherein the X-ray radiation device generates first and second pulses of photons in an alternating manner, wherein the photons in the first pulse has the first energy level and the photons in the second pulse has the second energy level.

6. The apparatus according to claim 5, wherein the detection device forms first and second images in an alternating manner, the first image corresponding to the spatial distribution of received photons having the first energy level during a first interval of time that corresponds to the duration of the first pulse, the second image corresponding to the spatial distribution of received photons having the second energy level during a second interval of time that corresponds to the duration of the second pulse.

7. A method for measurement of flow velocity of a multi-phase fluid mixture comprising at least a gaseous phase and a liquid phase, the method comprising:

generating an X-ray radiation comprising a beam of photons to irradiate the mixture spatially along a section of flow of the mixture, wherein the generating of a beam of photons comprises generating photons at a first energy level and a second energy level, wherein for the first energy level, the photon absorption coefficients for two different phases contained in the mixture are substantially equal, and wherein for the second energy level, the photon absorption coefficients for the two phases of the mixture are different, spatially receiving photons generated at both the first and second energy levels upon emanating from the section of flow of the mixture over a single two dimensional array of detector elements arranged along a plane at different intervals of time, and forming a two-dimensional image of a spatial distribution of the received photons for each said interval of time, and determining a flow velocity of each of the phases of the fluid mixture based on a temporal sequence of the images of the spatial distributions of the received photons, wherein the plane extends along a first direction parallel to a flow direction of the mixture and a second direction transverse to the flow direction.

8. The method according to claim 7, further comprising determining a spatial density distribution of each of the phases of the mixture based on the images of the spatial distribution of photons received over the two-dimensional area.

9. The method according to claim 7, wherein the generating of the beam of photons comprises generating first and second pulses of photons in an alternating manner, wherein the photons in the first pulse has the first energy level and the photons in the second pulse has the second energy level.

10. The method according to claim 9, comprising forming first and second images of the received photons in an alternating manner, the first image corresponding to the spatial distribution of received photons having the first energy level during a first interval of time that corresponds to the duration of the first pulse, the second image corresponding to the spatial distribution of received photons having the second energy level during a second interval of time that corresponds to the duration of the second pulse.

11. The method according to claim 7, wherein the determining of the flow-rate of each of the phases of the mixture is based on cross-correlation of the temporal sequence of images of the spatial distributions of received photons.

12. The method according to claim 7, further comprising determining a displacement of the at least one liquid phase as a whole and a rate of change of composition of the at least one liquid phase transverse to the flow direction, based on the temporal sequence of two-dimensional images.

13. An apparatus for measurement of flow velocity of a multi-phase fluid mixture comprising at least a gaseous phase and a liquid phase, the apparatus comprising:

an X-ray radiation device for generating a beam of photons to irradiate the mixture spatially along a section of flow of the mixture, a detection device comprising a two-dimensional array of detector elements arranged on a plane that are spatially configured for receiving photons emanating from the section of flow of the mixture over a two-dimensional area along the plane at different intervals of time, and for forming a two-dimensional image of a spatial distribution of the received photons for each said interval of time, and an analysis device for determining a flow velocity of each of the phases of the fluid mixture based on a temporal sequence of the images of the spatial distributions of the received photons, wherein the plane extends along a first direction parallel to a flow direction of the mixture and a second direction transverse to the flow direction, and wherein based on the temporal sequence of two-dimensional images, the analysis device determines a displacement of the at least one liquid phase as a whole and a rate of change of composition of the at least one liquid phase transverse to the flow direction.

\* \* \* \* \*